United States Patent [19]

Ippolito et al.

[11] Patent Number: 5,290,809
[45] Date of Patent: Mar. 1, 1994

[54] METHODS FOR THE TREATMENT OF SEBORRHEIC DERMATITIS

[75] Inventors: Ferdinando Ippolito; Siro Passi, both of Rome, Italy

[73] Assignee: Istituto Fisioterapici Ospitalieri, Italy

[21] Appl. No.: 892,190

[22] Filed: Jun. 2, 1992

[30] Foreign Application Priority Data

Jun. 18, 1991 [IT] Italy ............................ RM91A000435

[51] Int. Cl.$^5$ ............................................. A61K 31/355
[52] U.S. Cl. ..................... 514/458; 424/702; 514/562; 514/864
[58] Field of Search ................ 424/702; 514/458, 562, 514/864

[56] References Cited

U.S. PATENT DOCUMENTS 4,613,622  9/1986  Moeller et al. ...................... 514/718

FOREIGN PATENT DOCUMENTS 2244468  4/1975  France .

8301196  4/1983  PCT Int'l Appl. .

OTHER PUBLICATIONS

Brenner, S. and Horwitz, C., "Possible Nutrient Mediators in Psoriasis and Seborrheic Dermatitis", *Wld Rev. Nutr. Diet.*, vol. 55, pp. 165–182, 1988.

*Primary Examiner*—Leonard Schenkman
*Attorney, Agent, or Firm*—Andrus, Sceales, Starke & Sawall

[57] ABSTRACT

A pharmaceutical product to be used as an adjuvant treatment of seborrheic dermatitis even in HIV positive subjects is disclosed. The pharmaceutical product makes use of methionine, vitamin E and selenium as active principles which directly or indirectly provide a protective response to the damage caused by lipoperoxidation. The pharmaceutical product, in combination with a diet rich in PUFA-PL (polyunsaturated fatty acids of phospholipids), causes skin homeostasis to be restored and the symptoms of skin dermatitis to regress.

2 Claims, No Drawings

METHODS FOR THE TREATMENT OF SEBORRHEIC DERMATITIS

The present invention relates to a pharmaceutical preparation which can be used in the dermatologic field and, more particularly, as an adjuvant treatment of seborrheic dermatitis even in HIV positive subjects.

Seborrheic dermatitis has been referred to as a marker of AIDS. Of course it should be appreciated that it does not have the same marker function performed with a greater specificity by ulcerative chronic herpes simplex, oral hairy leukoplakia and epidemic kaposi. However, because the epidemiologic incidence of seborrheic dermatitis in HIV positive subjects is 30% on the average, its presence is a significant indicator of HIV infection.

Recent research reported in the literature (F. Ippolito et al.: "Seborrheic-like dermatitis in subjects having acquired immunodeficiency", Giorn. It. Ann. Ven., Vol. 124, 1989; F. Ippolito et al.: "Insufficient haematic levels of the polyunsaturated fatty acids of the phospholipids, vitamin E and glutathione peroxidase as likely risk factors in the onset and development of the acquired immunodeficiency syndrome", Giorn. It. Derm. Ven. Vol. 125, 1990), have pointed out that the haematic levels of vitamin E, polyunsaturated fatty acids of the phospholipids (PUFA-PL) and glutathione peroxidase (GSH-PX) are considerably reduced in subjects having seborrheic dermatitis as well as in HIV positive subjects affected and non-affected by seborrheic dermatitis compared to checked healthy subjects of the same age.

PUFA-PL play a vital role in the physiology of the cells including the epidermal cells as they keep the integrity and the fluidity of the cell membranes and contribute to the normal development of the cellular physiologic processes through the biosynthesis of the regulating eicosanoids (prostaglandins and leucotrienes) and in association with other messengers.

PUFA-PL easily peroxidize. The two major protective agents in vivo against damage from lipoperoxides are vitamin E and GSH-PX. Thus, as reported in a number of printed papers of the literature, the primary site of the pathologies due to deficiency of vitamin E is the cell membrane.

GSH-PX is adapted to modulate the radical reactions with chains supported by hydroperoxides. Since selenium is the prosthetic group of the enzyme, this element is very important for the neutralization in vivo of damage due to lipoperoxidative processes.

On the basis of such clinical-epidemiological, biochemical remarks, the inventors have noted that the therapeutic association of vitamin E, selenium and methionine administered in suitable proportion and dosage is able to improve general and cutaneous cell homeostasis.

Firstly, methionine is the precursor of reduced glutathione, the main non-lipidic membrane antioxidant which is the essential component of the glutathione peroxidase, of which selenium is the prosthetic group. The choline is indispensable in the biosynthesis of the lecithin or phosphatidylcholine which is the major component of the phospholipids.

The integration of vitamin E, the main lipidic antioxidant directly present in the membranes, and selenium by compensating the respective hematochemical deficiencies completes the action of the methionine on the hepatic functional capacity, thus making it possible to provide a valid protective response to the damage due to lipoperoxidation and as a consequence to restore the cutaneous homeostasis with the regression of the symptomatology of the seborrheic dermatitis.

The administration of vitamin E and selenium cannot make up for the reduction of the polyunsaturated acids of the phospholipid fraction. There is needed the direct contribution of a diet rich in PUFA-PL present in the red meat, the cell membranes of which are generally characterized by high levels of eicosanoic acid, precursor of prostaglandins and leucotrienes playing an important role in the cell homeostasis.

Considering the above-cited data, the pharmaceutical preparation according to the present invention is proposed with the following formulation for a capsule:

| Active principles: | |
|---|---|
| L-methionine | 150 mg |
| d,L-α-tocopherol equivalent to basic vitamin E | 75 mg |
| selenium-D-L-methionine 0,65 mg equivalent to selenium | 0.030 mg |
| Excipients | |
| capric-caprilic trilgyceride | 152 mg |
| glyceryl palmitostearate | 5.000 mg |
| soybean lecithin | 2.500 mg |

Research has emphasized that the advisable dosage ranges between a minimum of 4 and a maximum of 8 capsules a day.

We claim:

1. A method for the treatment of seborrheic dermatitis in a subject, including HIV positive subjects, with a pharmaceutical preparation comprising, seborrheic dermatitis reducing amounts of methionine, vitamin E and selenium and a pharmaceutically-acceptable excipient, wherein the selenium is present in an amount ranging between 0.015 and 0.025% by weight of the methionine, characterized in that the daily administration to said subject of said active principles ranges between 600 and 1200 mg of L-methionine, 300–600 mg of vitamin E and 0.120–0.240 mg of selenium.

2. A method for the treatment of seborrheic dermatitis in a subject, including HIV positive subjects, with a pharmaceutical preparation comprising, in capsule form,

| Active principles: | |
|---|---|
| L-methionine | 150 mg |
| d,L-α-tocopherol equivalent to basic vitamin E | 75 mg |
| selenium-D-L-methionine 0.65 mg equivalent to selenium | 0.030 mg |
| Excipients | |
| capric-caprilic triglyceride | 152 mg |
| glyceryl palmitostearate | 5.000 mg |
| soybean lecithin | 2.500 mg | characterized in that the daily administration to said subject of said active principles ranges between 600 and 1200 mg of L-methionine, 300–600 mg of vitamin E and 0.120–0.240 mg of selenium through the administration of 4–8 of said capsules per diem.

* * * * *

UNITED STATES PATENT AND TRADEMARK OFFICE
CERTIFICATE OF CORRECTION

PATENT NO. : 5,290,809
DATED : March 1, 1994
INVENTOR(S) : Ferdinando Ippoliti et al It is certified that error appears in the above-indentified patent and that said Letters Patent is hereby corrected as shown below:

On the title page, item [73]: Assignee:

Delete "Istituto" and substitute therefor --- Istituti---

Signed and Sealed this

Seventh Day of November, 1995

Attest:

BRUCE LEHMAN

*Attesting Officer*         *Commissioner of Patents and Trademarks*